(12) United States Patent
Shelley et al.

(10) Patent No.: US 6,906,327 B2
(45) Date of Patent: *Jun. 14, 2005

(54) METHOD OF MEASURING AMOUNT OF CHEMICAL CURE AND AMOUNT OF SURFACE CONTAMINATION USING INFRARED ABSORBANCE

(75) Inventors: Paul H. Shelley, Lakewood, WA (US); Diane R. LaRiviere, Seattle, WA (US)

(73) Assignee: The Boeing Company, Chicago, IL (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/304,627

(22) Filed: Nov. 26, 2002

(65) Prior Publication Data

US 2004/0099806 A1 May 27, 2004

(51) Int. Cl.[7] .................................................. G01J 5/02
(52) U.S. Cl. ............................. 250/339.01; 250/338.1; 250/336.1
(58) Field of Search ......................... 250/339.01, 338.1, 250/336.1

(56) References Cited

U.S. PATENT DOCUMENTS

| | | | |
|---|---|---|---|
| 4,527,062 A | | 7/1985 | Novinson |
| 4,625,114 A | * | 11/1986 | Bosacchi et al. ......... 250/341.4 |
| 5,091,647 A | * | 2/1992 | Carduner et al. ....... 250/339.09 |
| 5,142,151 A | | 8/1992 | Varnell et al. |
| 5,208,648 A | * | 5/1993 | Batchelder et al. ...... 356/237.1 |
| 5,381,228 A | | 1/1995 | Brace |
| 6,330,387 B1 | * | 12/2001 | Salamon et al. ............ 385/129 |
| 6,441,375 B1 | * | 8/2002 | Joseph et al. .......... 250/339.09 |
| 6,784,431 B2 | * | 8/2004 | Shelley et al. ........... 250/341.8 |
| 2003/0001119 A1 | * | 1/2003 | Takezawa et al. ..... 250/559.45 |
| 2003/0230720 A1 | * | 12/2003 | Shelley et al. ........... 250/341.8 |
| 2003/0232448 A1 | * | 12/2003 | Shelley et al. .............. 436/164 |
| 2004/0099807 A1 | * | 5/2004 | Shelley et al. ......... 250/339.01 |

OTHER PUBLICATIONS

X Ramis et al: "Polyurethane–unsaturated polyester interpenetrating polymer networks: thermal and dynamic mechanical thermal behaviour," Polymer 42 (2001) 9469–9479.

* cited by examiner

*Primary Examiner*—David Porta
*Assistant Examiner*—Christine Sung
(74) *Attorney, Agent, or Firm*—Black Lowe & Graham PLLC (57) ABSTRACT

Amount of coating cure or contamination is determined. An infrared beam is transmitted into a crystal. The beam reflects off an internal face at an angle higher than critical reflection angle to generate total reflection at the crystal face. The beam exits the crystal, is filtered at two wavelengths, and is detected to give values $I_{o1}$ and $I_{o2}$ of infrared energy reflected without coating. A coated sample contacts an outside face of the crystal. An evanescent wave penetrates the sample where the beam reflects from internal crystal face. The beam is partially absorbed by sample, exits the crystal, is filtered at two wavelengths, and is detected to give values $I_{c1}$ and $I_{c2}$ of infrared energy reflected with coating. Absorbance values A1 and A2 at two wavelengths are $A1 = -\log_{10}(I_{c1}/I_{o1})$ and $A2 = -\log_{10}(I_{c2}/I_{o2})$. Amount of cure or contamination is proportional to ratio or difference between A1 and A2.

33 Claims, 8 Drawing Sheets

METHOD OF MEASURING AMOUNT OF CHEMICAL CURE AND AMOUNT OF SURFACE CONTAMINATION USING INFRARED ABSORBANCE

RELATED APPLICATIONS

This patent application is related to a concurrently-filed patent application entitled "Method of Measuring Thickness of an Opaque Coating Using Infrared Absorbance" and bearing attorney docket number BOEI-1-1078, which is hereby incorporated by reference.

FIELD OF THE INVENTION

This invention relates generally to measuring chemical amounts and, more specifically to measuring amount of chemical cure and/or amount of surface contamination.

BACKGROUND OF THE INVENTION

Paint, primer, sealants and other coatings usually undergo a chemical cure after being applied on a substrate, such as metal or plastic. The time allowed for curing these materials varies from a few minutes to many hours, and it is usually important to allow the cure to proceed to near completion before subsequent processes are performed. In the case of many coatings, it is important to apply a next coating before a previous coating is completely cured in order to assure good bonding between coating layers. In other cases, it is important for a coating to be completely cured before placement into service of a coated item, such as a fuel tank or a water tank.

However, determining state of cure or amount of cure may be difficult. Current coating cure tests include physical tests, such as a "dry-to-tape" test for primers and top coat paints and a tack-feel test for other coatings. These tests can be quite subjective and often may not give desired results.

Surface cleanliness has become more important because paint and primer systems have included more solids and less solvent over the past 10 years due to environmental regulations. High solids paint systems are more sensitive to surface contamination than are high solvent paint systems. Further, high solids paint systems may fail to adhere to a surface when a fairly low level contamination is present on the surface. For example, sufficient adherence of paint or primer to dielectric materials such as plastic and non-metallic surfaces depends upon cleanliness of the surface.

Known surface contamination measurement methods now available include portable fourier transform infrared (FT-IR) spectrometers, but these systems are heavy, bulky, and often cannot reach into a confined space. Surface contamination measurements with FT-IR systems require expert interpretation and detailed knowledge of system software and hardware.

Therefore, there exists an unmet need in the art for a simple and reliable method of measuring chemical cure and surface contamination.

SUMMARY OF THE INVENTION

The present invention provides a simple and reliable method for measurement of the amount of cure of a coating on a substrate and/or the amount of surface contamination on a coating on a substrate. The invention may be employed in an in-line production facility or may be used intermittently as desired. The process may be used to provide a quantitative measurement, such as cure amount or an amount of surface contamination, or a qualitative measurement, such as a go or no-go result.

A nondestructive method is provided for efficiently determining an amount of cure for paints, primers, sealants and coatings as well as determining an amount of contamination of a surface. According to one embodiment of the present invention, an infrared beam is transmitted into an infrared-transparent wave guide crystal with no sample present and a reflection is formed on an internal crystal face at a predetermined reflection beam angle. The infrared beam is reflected off the internal face of the crystal at an angle higher than the critical reflection angle in the crystal to generate a total reflection at the crystal face. Under these conditions, an evanescent wave extends into the air that contacts the outside of the crystal face, and none the evanescent wave is absorbed. The infrared beam exits the crystal, is filtered with two filters at two predetermined wavelengths, and is detected by two detectors to give two base reference values $I_{o1}$ and $I_{o2}$ of infrared energy reflected without a coating. A coated sample to be measured is put in intimate contact with an outside face of the infrared-transparent crystal and an evanescent wave penetrates the sample where the infrared beam reflects from the internal crystal face. The infrared beam is attenuated by being partially absorbed by the sample. The attenuated infrared beam exits the infrared-transparent crystal and is filtered by the two filters and detected by the two detectors to give values $I_{c1}$ and $I_{c2}$ of infrared energy reflected with the coating. Infrared absorbance values A1 and A2 at the two wavelengths are calculated according to the relationships $A1=-\log_{10}(I_{c1}/I_{o1})$ and $A2=-\log_{10}(I_{c2}/I_{o2})$. Depending upon wavelengths chosen, either a ratio of or a difference between the absorbance values A1 and A2 at the two wavelengths is calculated, and the amount of cure or contamination is proportional to the ratio of or difference between the absorbance values A1 and A2. A calibration is done with traditionally measured cure or contamination amount standards to get an equation from which cure or contamination amount is calculated from infrared absorbance measurements on production parts.

BRIEF DESCRIPTION OF THE DRAWINGS

The preferred and alternative embodiments of the present invention are described in detail below with reference to the following drawings.

DETAILED DESCRIPTION OF THE INVENTION

The present invention provides a method for nondestructively determining an amount or degree of chemical cure for coatings such as paint, primer, sealants, or other coatings, or for nondestructively determining an amount of surface contamination, by correlating a relationship such as ratio of or difference between infrared absorbance of the coating at two predetermined wavelengths to the amount of cure or contamination. The cure amount measurement can be made in percent completion of the cure process or any other appropriate measure. The measurement of amount of contamination on a surface or degree of cleanliness of a surface is normally expressed in terms of units such as milligrams per square foot of contamination found. Both measurements entail calibrating the infrared absorbance of the one or more bands, at specific wavelengths, to the amount of cure or contamination.

Figure 1:
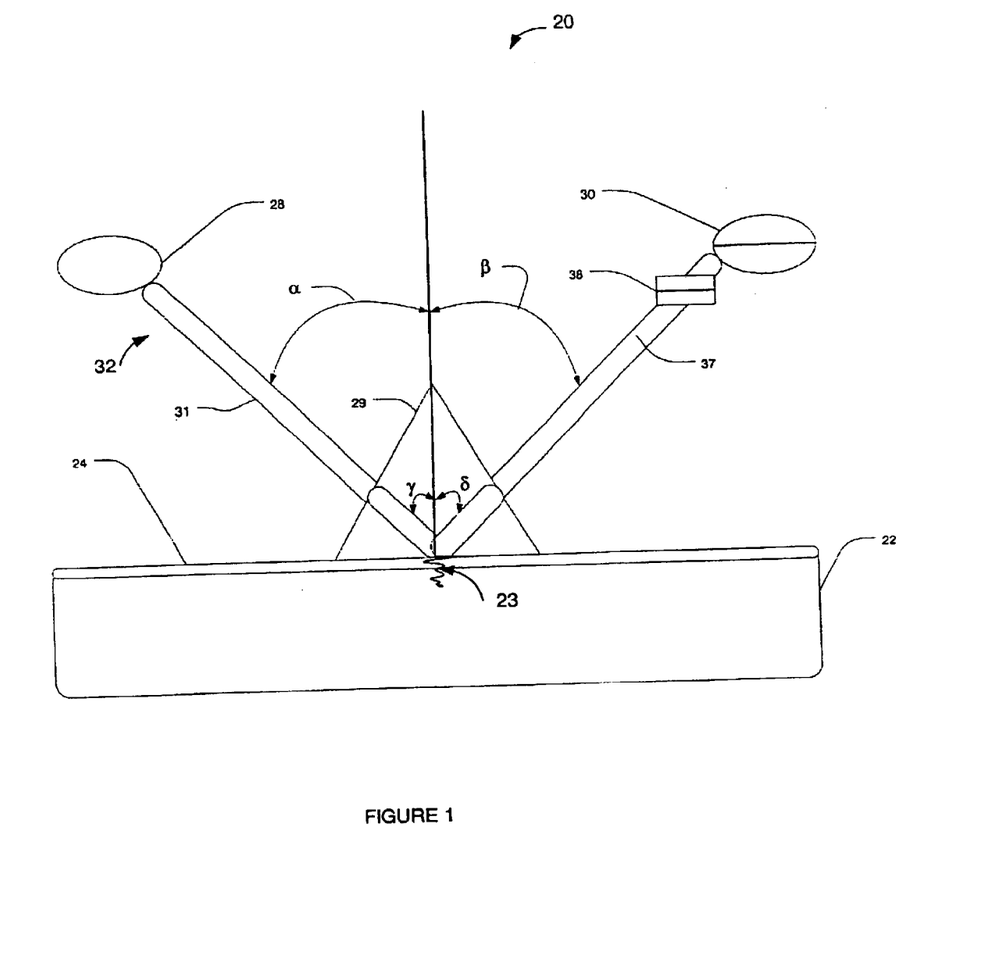
FIG. 1 is a side view of a testing setup according to the present invention.

By way of overview and with reference to FIG. 1, one presently preferred embodiment of the present invention determines amount of cure or contamination using a testing setup 20. Initially, a base reference value of infrared energy reflected by an infrared-transparent crystal 29 with no coated sample is determined as follows. An infrared transmission beam 31 is transmitted from an infrared source 28 along a predetermined incident beam path 32 and into the crystal 29. The crystal 29 is not in contact with any sample. The infrared beam 31 is transmitted in such a fashion to form a reflection on an internal face of the crystal 29 at an angle γ that is greater than the critical reflection angle for the crystal 29 and sample being used. The transmission beam 31 is reflected off the internal crystal face. The infrared beam 37 that exits the crystal 29 is filtered by a pair of filters 38 and is detected by a pair of infrared detectors 30 that are set to different wavelength ranges. A substrate 22 with a sample of a coating or contamination 24 is put into contact with the crystal 29 and the infrared beam 31 is transmitted into the crystal 29 as described above. At the point of reflection an infrared evanescent wave 23 is set up in the sample and is selectively absorbed by the sample depending upon the chemical nature of the sample. The infrared beam 37 is attenuated by the amount of the evanescent wave's energy that is absorbed in the sample in contact with the crystal 29. A comparison is made of the infrared energy of the attenuated infrared beam 37 and the infrared energy of the base reference value to determine two different absorbance values. These absorbance values are correlated to absorbance values of known cure states or known contamination amounts and the amount of cure or contamination is determined. Specific details of the testing setup 20 are described with more particularity below.

In one presently preferred, non-limiting embodiment for determining an amount of cure described herein for illustrative purposes only, the measurement is conducted for a coating 24 of polyurethane paint on a metallic substrate 22, such as paint that is suitably used on aircraft. However, measurements of other coatings 24 such as other paints, primers, sealants and coatings are considered within the scope of this invention, such as, without limitation, epoxy primers, polysulfide sealants, and fuel tank vapor barrier coatings. It will be appreciated that the present invention may be used to measure cure for a large variety of coatings 24 and sealants that undergo a chemical curing process as well as coatings and sealants that simply dry to cure. In order to measure the amount of cure for other coatings 24 and sealants that are not illustrated herein, one simply selects suitable wavelength infrared absorbance bands that change with the curing process for each different material.

In another presently preferred embodiment, given by way of non-limiting example for illustrative purposes only, cleanliness is measured of a sample of oil on a primer surface, such as aircraft fuel on epoxy primer. Additionally, given by way of non-limiting example, cleanliness measurements may be made of other samples or coatings 24 such as without limitation silicone and teflon release agents on a substrate 22 of dielectric material. The present invention may be used to measure contamination of many other surfaces that are contaminated by contaminants including, but not limited to, silicones, teflons, hydraulic oils, lubricants, engine oils, and the like. It will also be appreciated substrates other than dielectric materials may be suitably measured for presence of contamination by the present invention. However, measurement of contamination of dielectric substrates is presently preferred. In order to measure the amount of contamination for other contaminants that are not illustrated herein, one simply selects suitable wavelength infrared absorbance bands that change with each different contaminant. For each cure or cleanliness measurement, a suitable, predetermined pair of wavelength bands is used and calibration data for those wavelengths are determined.

The testing setup 20 will be described in the context of measurement of chemical cure. After the chemical cure context has been explained, an explanation will be given regarding contamination measurement.

In a presently preferred embodiment, the testing setup 20 is suitably a simple infrared filter spectrometer system, including the infrared source 28, infrared beam optics, the crystal 29 that contacts the sample or coating 24, the filter 38, the detector 30, and a data system (not shown). A non-limiting example of a simple infrared filter system is a Coating Weight Reader produced by Personal Instruments. However, it will be appreciated that other infrared systems are employable with the testing setup 20, such as, without limitation, standard Fourier transform infrared spectrometers and infrared imaging systems. Non-limiting examples of standard Fourier transform infrared spectrometers are a Thermo Nicolet 760 FT-IR spectrometer system fitted with a diamond crystal attenuated total reflectance (ATR) accessory and a Surface Optics Corporation SOC400 portable FT-IR spectrometer with a diamond ATR attachment. Non-limiting examples of infrared imaging systems employable with the present invention include ImageMax® produced by Thermo Nicolet. It will be appreciated that the various infrared systems may be as used in-line production elements or may be a portable, hand-held arrangement.

In an example of cure measurement, the infrared beam 31 is suitably transmitted as a broadband mid-infrared light beam (2.5 to 25 microns typically). In a preferred embodiment, the reflected beam 37 is suitably filtered by the pair of filters 38 at two presently preferred wavelength bands with center wavelengths of approximately 4.41 microns ($\mu$m) and 5.82 microns ($\mu$m). The filters 38 may act on either the transmitted beam 31 or the reflected beam. It will be appreciated, however, that the optimal wavelength may deviate from the preferred wavelength depending on the material to be measured. Wavelength ranges from about 4.21 $\mu$m to about 4.61 $\mu$m and from about 5.62 $\mu$m to about 6.02 $\mu$m have been found to provide acceptable infrared absorbance characteristics and are to be considered within the scope of this invention for this example. Further, it will be appreciated that when using either standard infrared spectrometer or infrared imaging systems, the filters 38 may suitably be implemented by hardware or software performing the same filtering function. When the detected infrared beam 31 has wavelength bands within these disclosed ranges, a relationship has been found to exist between a ratio of infrared absorbance of the 5.82 band to infrared absorbance of the 4.41 band and the amount of cure, as discussed in more detail below.

Figure 2A:
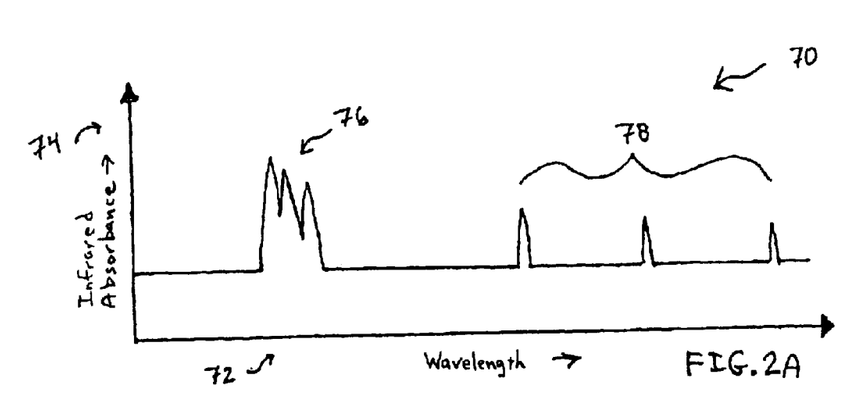
FIGS. 2A and 2B are graphs of absorbance versus frequency during chemical curing.

According to the present invention, measurement of chemical cure takes advantage of changes in absorbance over time as chemical changes take place during the cure process. FIG. 2A shows a graph 70 of wavelength (λ) along an X-axis 72 versus infrared absorbance along a Y-axis 74 at a time near the beginning of a chemical cure process. First absorbance peaks 76 arise due to absorbance at a first wavelength by end groups of polymeric chains that are present at the beginning of the cure process. Second absorbance peaks 78 arise due to absorbance at a second wavelength that is higher than the first wavelength by links that are present at the beginning of the cure process.

Figure 2B:
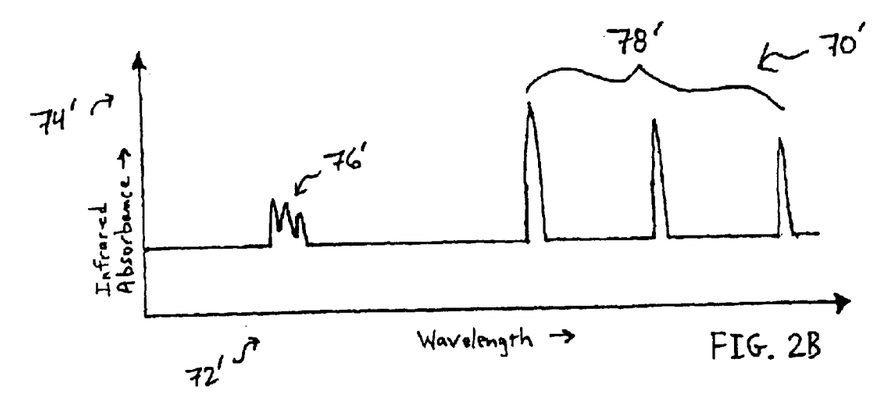

Over time, cross-linking polymerization during chemical curing forms bonds that link together polymeric chains. FIG. 2B shows a graph 70' of wavelength along an X-axis 72' versus infrared absorbance along a Y-axis 74' at a time later in the chemical cure process. First absorbance peaks 76' arise due to absorbance at the first wavelength by end groups that are present later in the cure process. Second absorbance peaks 78' arise due to absorbance at the second wavelength by links that are present later in the cure process. During the cure process, the end groups that gave rise to the first absorbance peaks 76 (FIG. 2A) go away because cross links form between the end groups. That is, as cross links form between end groups, the end groups are no longer at ends of chains. As a result, later in the cure process fewer end groups exist and more cross-links exist. Therefore, the first absorbance peaks 76' have a lower value than do the first absorbance peaks 76 (FIG. 2A). Conversely, the second absorbance peaks 78' have a greater value than do the second absorbance peaks 78 (FIG. 2A). It will be appreciated that the first and second wavelengths may vary depending upon the chemical undergoing the cure process. For example, given by way of non-limiting example, for curing of polyurethane paint the first wavelength is suitably in a range from around 4.21 μm to about 4.61 μm and the second wavelength is suitably in a range from about 5.62 μm to about 6.02 μm. In one presently preferred embodiment, the first wavelength is around 4.41 μm and the second wavelength is around 5.82 μm. As another non-limiting example, for curing of epoxy primer the first wavelength is around 6.86 μm and the second wavelength is around 7.34 μm. It will be appreciated that other wavelengths may be selected as desired for measuring cure amount of other materials.

Figure 2C:
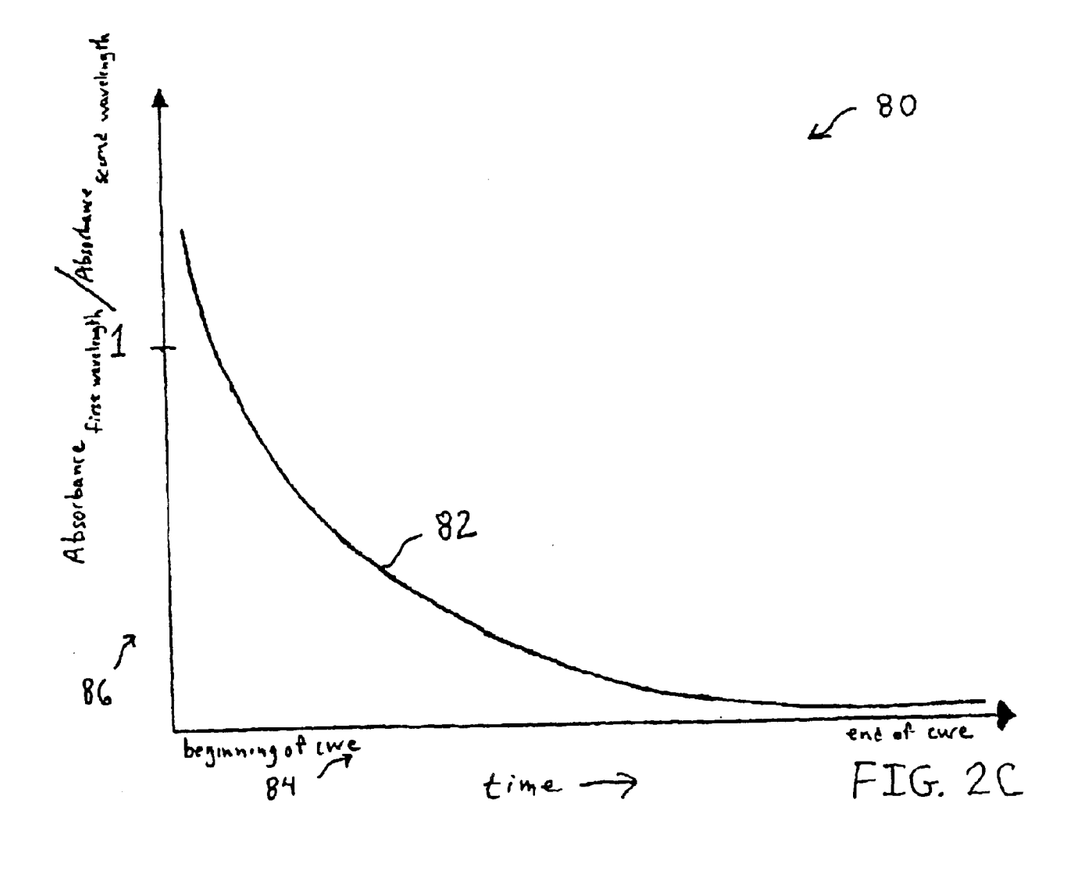
FIG. 2C is a graph of absorbance ratios versus time for chemical curing'

Changes in absorbance at the first and second wavelengths over time during the cure process advantageously provide an indication of progress of the cure process, as shown in FIG. 2C. Referring now to FIGS. 2A, AB, and 2C, a graph 80 shows a curve 82 over time along an X-axis 84 of a ratio of absorbance at the first wavelength to absorbance at the second wavelength along a Y-axis 86. As shown in FIG. 2C, the curve 82 indicates that absorbance at the first wavelength is greater than absorbance at the second wavelength at the beginning of the cure process. That is, the first absorbance peak 76 is greater than the second absorbance peak 78 at the beginning of the cure process. Accordingly, a ratio of the first absorbance peak 76 to the second absorbance peak 78 is greater than one. As the cure process progresses, the first absorbance peak 76' becomes less than the second absorbance peak 78'. Accordingly, a ratio of the first absorbance peak 76' to the second absorbance peak 78' becomes less than one. When the ratio of the first absorbance peak 76' to the second absorbance peak 78' approaches a predetermined value or, alternately, approaches a stabilized value that has stopped appreciably lowering, the cure process may be considered complete.

Figures 3A, 3B:
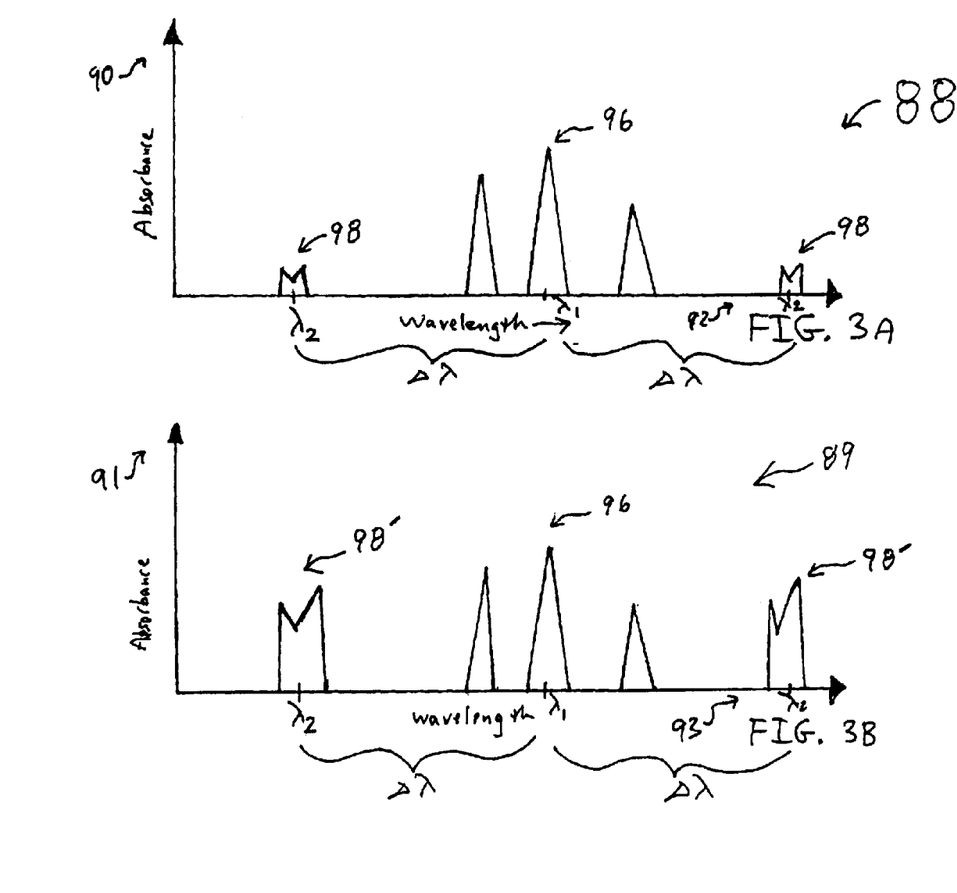
FIGS. 3A and 3B are graphs of absorbance versus frequency for a contaminated sample.

According to another embodiment of the present invention, measurement of amount of contamination takes advantage of changes in scattering as wavelength of infrared radiation varies. Referring now to FIGS. 3A and 3B, FIG. 3A shows a graph 88 of absorbance of infrared energy in an uncontaminated sample along a Y-axis 90 versus wavelength along an X-axis 92. FIG. 3B shows a graph 89 of absorbance of infrared energy in a contaminated sample along a Y-axis 91 versus wavelength along an X-axis 93. Advantageously, the present invention measures the infrared absorbance at two wavelengths to compensate for changes in infrared absorbance due to contamination. Referring now to FIG. 3A, absorbance peaks 96 are detected at a first wavelength $\lambda_1$ for the sample being measured. The first wavelength $\lambda_1$ occurs where absorbance is expected for the sample being measured. Absorbance peaks 98 are detected at a second wavelength $\lambda_2$ as a result of absorbance by the substrate. It will be appreciated that the absorbance peak 98 represents a reference measurement of substrate that is known to be uncontaminated. The second wavelength $\lambda_2$ is offset from the first wavelength $\lambda_1$ by a wavelength difference $\Delta\lambda$. It will be appreciated that the second wavelength $\lambda_2$ is suitably greater than the first wavelength $\lambda_1$ or is suitably less than the first wavelength $\lambda_1$, as desired for a particular application.

Referring now to FIG. 3B, the absorbance peak 96 at the first wavelength $\lambda_1$ remains unaffected by presence of contamination. However, absorbance peaks 98' at the second wavelength $\lambda_2$ increase (compared to the absorbance peaks 98 of FIG. 3A) due to contamination. Thus the absorbance peaks 98' result due to both the substrate and contamination. Comparing magnitude of the absorbance peak 96 at the first wavelength $\lambda_1$ to magnitude of absorbance peaks 98' at the second wavelength $\lambda_2$ provides an indication of presence of contamination. If the value of the absorbance peak 98' is greater than the value of the absorbance peak 98 (FIG. 3A), then contamination is indicated. However, if contamination is not present, then the value of absorbance at the second wavelength $\lambda_2$ will remain the same. That is, the magnitude of the absorbance peaks 98 and 98' are the same because they result only from absorbance by the substrate.

According to the present invention, this determination is made either by determining a ratio of magnitude of the absorbance peak 96 to magnitude of the absorbance peak 98'. If the ratio is greater than a ratio of magnitude of the absorbance peaks 96 to 98 for the reference, uncontaminated substrate, then presence of contamination is indicated. Alternately, the ratio may be made between the absorbance peaks 98' to 96 (and the absorbance peaks 98 to 96), in which case a decrease in the ratio indicates presence of contamination. Alternately, a difference between the magnitude of the absorbance peaks 96 and 98' may be compared to a difference between magnitude of the absorbance peaks 96 and 98 for the reference, uncontaminated substrate. Similarly, if the difference between the magnitude of the absorbance peaks 96 and 98' is greater than a difference of magnitude of the absorbance peaks 96 to 98 for the reference, uncontaminated substrate, then presence of contamination is indicated. Given by way of non-limiting example, for measuring hydrocarbon contamination on polyurethane paint the first wavelength $\lambda_1$ is suitably in a range from around 6.3 μm to around 6.5 μm and is preferably around 6.4 μm, and the second wavelength $\lambda_2$ is suitably in a range either from around 3.37 μm to around 3.47 μm and is preferably around 3.42 μm. Further, for measuring silicone contamination on polyurethane paint the first wavelength $\lambda_1$ is suitably in a range from around 6.3 μm to around 6.5 μm and is preferably around 6.4 μm, and the second wavelength $\lambda_2$ is suitably in a range either from around 9.0 μm to around 10.0 μm and is preferably around 9.5 μm. As further non-limiting examples, for measuring hydrocarbon contamination on epoxy primer the first wavelength $\lambda_1$ is suitably around 8.1 μm and the second wavelength $\lambda_2$ is suitably around 3.4 μm. For silicone contamination on epoxy primer the first wavelength $\lambda_1$ is suitably around 8.1 μm and the second wavelength $\lambda_2$ is suitably around 9.5 μm.

Referring back to FIG. 1, the broadband infrared beam 31 is generated by the infrared source 28. The infrared source 28 is any acceptable source of infrared energy known in the art that can produce the infrared beam 31 having the desired wavelength region. One suitable example of a preferred embodiment of the infrared source is the ReflectIR-PIN source made by Ion Optics.

The infrared detectors 30 in the filtered systems described here are suitably arranged to detect the reflected beam 37. One suitable example of a preferred embodiment of the infrared detectors 30 is the Eltec Corp 406MAY-XXX where XXX indicates the filters that are used with the detectors 30.

The crystal 29 is suitably any crystal known in the art acceptable for attenuated total reflectance (ATR) accessories. Use of the crystal 29 is desirable to enable measurement of reflected energy from non-metallic surfaces, such as dielectric material. The crystal 29 is selected such that the refractive index n for the crystal 29 is greater than the refractive index n of the sample to be measured. This enables internal reflection to be established within the crystal 29. Given by way of non-limiting example, the crystal 29 is suitably any diamond ATR accessory known in the art.

An evanescent wave is induced and is transmitted from the crystal 29 to the sample in contact with the crystal 29. A finite amount of the evanescent wave's energy is absorbed in the sample in contact with the crystal 29. Thus the magnitude of the infrared energy of the reflected beam 37 is attenuated from the magnitude of the infrared energy of the beam 31 by the amount of the evanescent wave's energy that is absorbed in the sample in contact with the crystal 29.

It will be appreciated that the crystal 29 is not depicted to scale in FIG. 1; rather, the crystal 29 is shown greatly enlarged to clearly depict raypaths of the infrared beams 31 and 37. The infrared beam 31 and the crystal 29 define a size of a spot being measured on the coating 24 of the sample that contacts the crystal 29. It is possible for the beam 31 and the crystal 29 to be arranged so there are multiple infrared beam reflections on the crystal 29 and thus multiple evanescent waves that penetrate the sample. In one presently preferred embodiment, there is only one infrared beam reflection for measurement of chemical cure amount and surface contamination amount.

The incident beam path 32 is directed into the crystal 29 such that the incident beam angle α creates the desired refracted beam angle γ. In one presently preferred embodiment, the incident beam angle α, relative to normal, is preferably about 45 degrees to about 60 degrees. In a particular embodiment, the incident beam angle α is preferably about 45 degrees. A reflected beam angle β equals the incident beam angle α. As a result, the reflected beam angle β is preferably within a range of about 45 degrees to about 60 degrees from normal. In one presently preferred embodiment, the reflected beam angle β is preferably about 45 degrees. It will be appreciated that the critical reflection angle γ to achieve total reflection at the internal crystal face varies from the angle of incidence α due to refraction as the beam 31 enters the crystal 29. The critical reflection angle γ can be found with knowledge of the refractive index $n_1$ of the crystal and the refractive index $n_2$ of the coating 24 of the sample that contacts the crystal. The critical reflection angle γ is suitably found according to the relationship $\sin(\gamma) > n_2/n_1$. This sample method is commonly used by industry and research and is called attenuated total reflectance (ATR). Given by way of non-limiting example, $n_1$ for diamond is around 2.4, and $n_2$ for oil is around 1.5. So, $n_2/n_1 = 0.625$. Therefore, $\sin(\gamma)$ must be greater than 0.625. It will be appreciated that $\sin(39°) = 0.629$, and therefore $\sin(39°) > 0.625$. As a result, total internal reflection is achieved in this example when γ>39°.

Figure 4:
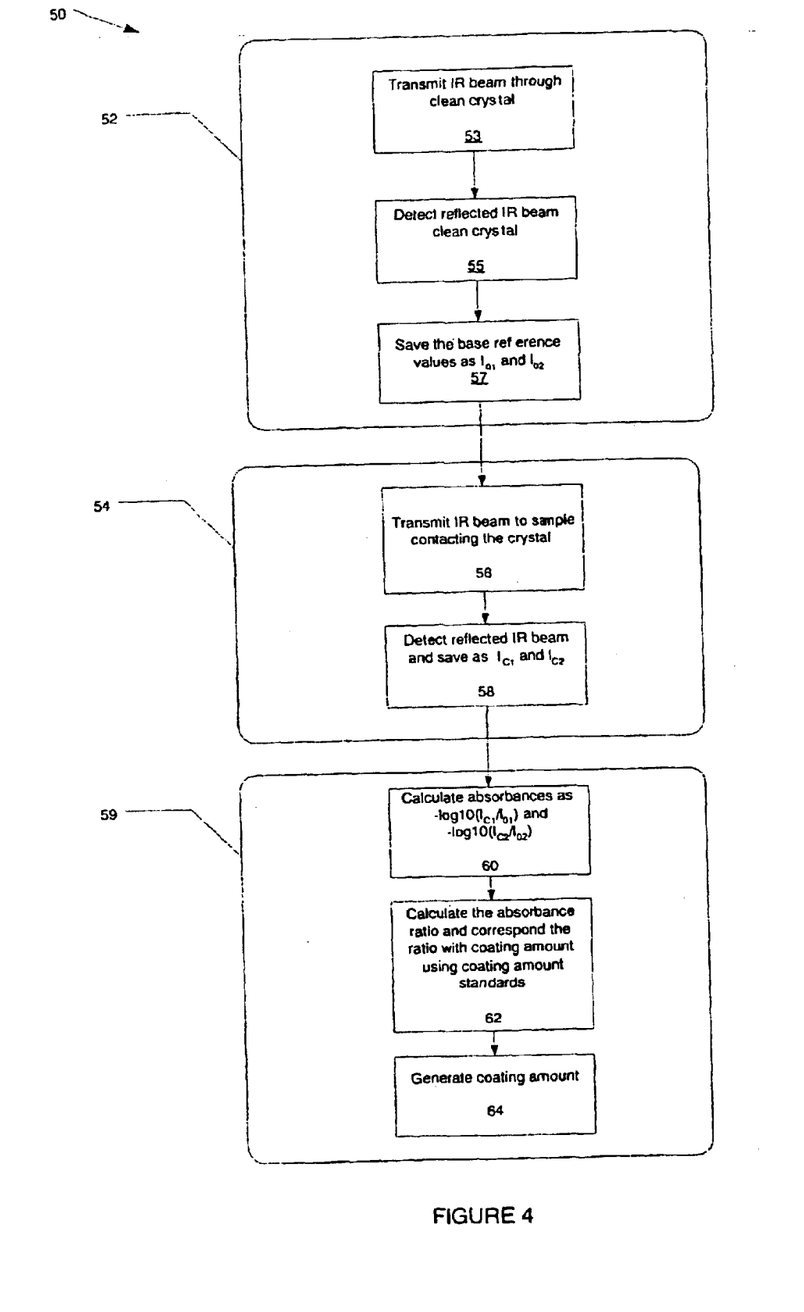
FIG. 4 is a flow chart of the testing process.

Referring now to FIGS. 1 and 4 and given by way of non-limiting example, a process 50 for determining the amount of cure for a polyurethane aircraft paint is illustrated. This process is substantially the same for a filtered infrared beam system, a standard infrared spectrometer system, or infrared imaging systems. Infrared energy base reference values $I_{o1}$ and $I_{o2}$ are determined at a block 52 for a clean crystal 29 with no sample or coating 24 contacting the crystal 29. This determines an amount of infrared energy being reflected without the sample or coating 24 contacting the crystal 29. At a block 53, the infrared beam 31 is transmitted into the crystal 29 to form a reflection at the internal crystal face. At a block 55, the beam 37 exiting the crystal 29 is filtered at two specific wavelengths as discussed above, and is detected by the two detectors 30 to yield the two base reference values of infrared energy $I_{o1}$ and $I_{o2}$. At a block 57 the reference infrared energy values are saved as $I_{o1}$ and $I_{o2}$.

After determining the base reference values $I_{o1}$ and $I_{o2}$, data collection on material with the partially cured polyurethane coating 24 begins at a block 54. As discussed above, the infrared-transparent crystal 29 is placed in physical contact with the sample or coating 24. The infrared beam 31 is transmitted into the crystal 29, and an evanescent wave is formed as discussed above. The resultant evanescent wave penetrates the paint sample coating 24 at a block 56 and is partially absorbed by the paint sample 24 to form an attenuated infrared beam 37 that exits the crystal 29. The exiting beam 37 is filtered and detected at a block 58 by the pair of filters 38 and the pair of detectors 30, respectively. Values of the infrared energy of the attenuated beam detected at the two wavelengths are saved as infrared energies $I_{c1}$ and $I_{c2}$. It will be appreciated that parameters such as the internal reflection beam angle γ, size of the spot, and overall incident beam path length are maintained substantially similar in both reference value determination and cure or contamination amount determination to limit potential errors.

Data calculation and compilation occurs at a block 59. The data compilation process includes calculation at a block 60 of absorbance values A1 and A2 at the first and second wavelengths of the cure sample 24 according to the relationships A1 equals $-\log_{10}(I_{c1}/I_{o1})$ and A2 equals $-\log_{10}(I_{c2}/I_{o2})$. At a block 62 a ratio A1/A2 is calculated. The compilation and calculation is suitably performed in a number of acceptable manners. For example, in one embodiment, it is performed by a processor or microprocessor (not shown) arranged to perform mathematical operations. Any processor known in the art is acceptable such as, without limitation, a Pentium®-series processor available from Intel Corporation or the like. The processor is suitably included within the infrared spectrometer and is also suitably provided as a stand-alone unit that is electrically connected to receive data from the infrared detectors 30. Alternately, the calculation is performed by an electronic computer chip or is performed manually. The results of the calculation yield an absorbance ratio A1/A2 that corresponds to the amount of cure.

The absorbance ratio measurement is repeated for many different degrees of cure from initial sample mixing to final cure with a sample system that is made as a standard for the type of paint, sealant or coating to be measured. The time from initial sample mixing is recorded with each absorbance ratio measurement. It is preferable that the standard be measured for the entire cure and the final cure be determined by a different reference method other than absorbance ratio (such as hardness, dry-to-tape, surface finish, and the like). An exemplary graph of such a series of absorbance ratio measurements over time is shown in FIG. 2C. The cure amount for each of the absorbance ratio measurements is found by measuring the time for the entire cure cycle and then calculating the percent of cure for each absorbance ratio measurement. The cure amount can also be given in terms of time to complete the cure, percent cure, or any other relevant units. At a block 64, the cure amount is generated. More specifically, a calibration is calculated for the cure amount by doing a plot or linear regression of the cure amount values versus the absorbance ratio values. This calibration can then be used to calculate cure amount directly from absorbance ratio values.

Amount of contamination is calculated in a similar manner except the standards are carefully applied and measured amounts of a known contaminant on the type of surface to be measured with the methods of the present invention. A non-limiting example of a contaminant measured by the present invention is aircraft fuel on an epoxy primer surface. Other contaminants that may be measured include silicone, teflon, hydraulic oil, lubricant, and engine oil, aircraft fuel, and cutting oil. In this case, the amount of fuel oil applied to each standard to be measured for the calibration data is carefully applied and measured with an alternative method after the absorbance values are measured. An example of an acceptable alternative method includes weighing the standard, measuring the absorbance values of the standard, removing the contamination with a solvent, and weighing the standard again. The contamination amount for the standard is calculated in terms of milligrams per square foot (mg/ft$^2$), and a calibration plot or regression is made using several standards as discussed above for cure amount measurement.

Figure 5:
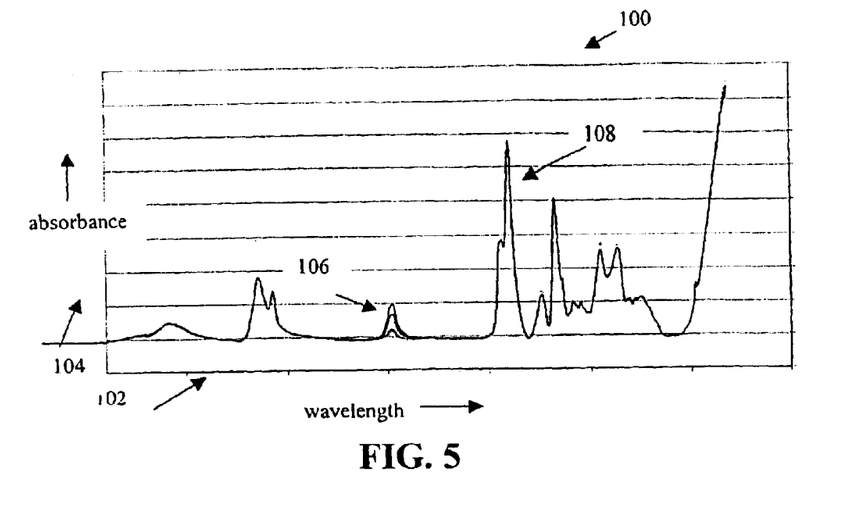
FIG. 5 is a graphical illustration of the relation between cure spectra and wavelength in accordance with the present invention.
Figure 6:
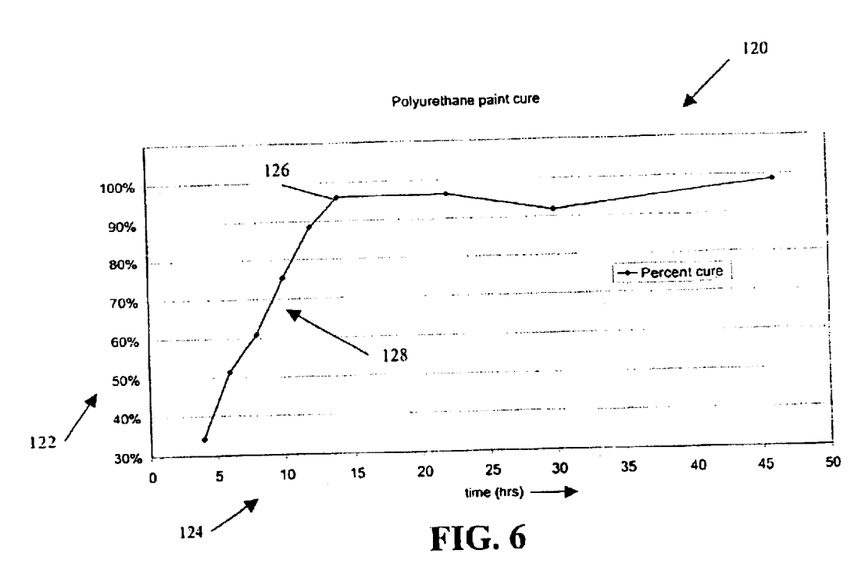
FIG. 6 is a graphical illustration of amount of cure over time in accordance with the present invention.

FIGS. 5 and 6 depict test data illustrating correlation between chemical cure amount and infrared absorbance ratio at the preferred wavelengths. It will be appreciated that FIGS. 5 and 6 represent experimental data generated by a bench-top infrared spectrometer. However, each trial was performed by the process of the present invention. It will also be appreciated that prior to testing, a reference determination using a clean crystal was made according to the present invention.

FIG. 5 shows a graph 100 of complete infrared spectra (that is, all wavelengths) for polyurethane topcoat paint measured according to the method 50 using a bench-top infrared spectrometer with an ATR crystal accessory. The graph 100 plots wavelength along an X-axis 102 versus absorbance ratio along a Y-axis 104. Several plots of the spectra were made over a total of 54 hours of cure time for the polyurethane topcoat paint. An absorbance peak 106 appears at the 4.41 $\mu$m band and an absorbance peak 108 appears at the 5.82 $\mu$m band. A Bio-Rad FTS-40 infrared spectrometer with a SensIR Durascope diamond ATR accessory was used to measure the spectra shown in the graph 100 and was set up to measure absorbance at 4.41 $\mu$m and 5.82 $\mu$m bands for the polyurethane topcoat paint.

Referring now to FIG. 6, a graph 120 shows percent cure along a Y-axis 122 versus time along an X-axis 124. The Y-axis 122 shows percent cure of the polyurethane paint measured in FIG. 5 based on a ratio of infrared absorbance at the 5.82 $\mu$m band to infrared absorbance at the 4.41 $\mu$m band. The cure is shown to be substantially complete at a point 126 that indicates about 97% cure at a time of around 14 hours. A substantially linear line 128 shows a substantially linear relationship between percent cure and time from an initial measurement at about 35% cured at around 4 hours to about 97% cured at around 14 hours.

Figure 7:
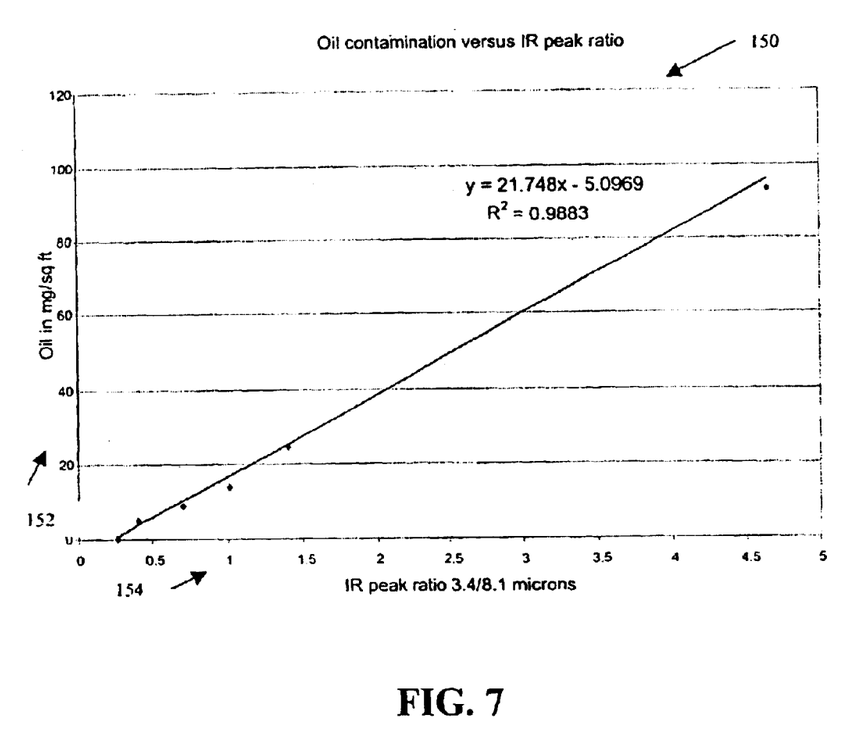
FIG. 7 is a graphical illustration of the relation between amount of contamination and infrared absorbance in accordance with the present invention.

Referring now to FIG. 7, a graph 150 shows oil contamination in mg/ft$^2$ on epoxy primer along a y-axis 152 versus ratio of absorbance peaks at wavelengths of 3.4 $\mu$m to 8.1 $\mu$m along an x-axis 154. The contamination was measured with a diamond ATR system in a Thermo Nicolet model 760 fourier transform infrared (FT-IR) spectrometer with a SensIR "Durasampler" diamond ATR accessory. Infrared spectra were made on an uncontaminated primered coupon and on 6 coupons that had epoxy primer with oil sprayed onto the primer. The level of contamination was measured on each coupon by weighing the coupon before and after the oil was sprayed onto them. Because the air brush that was used to spray the coupons with oil does not give perfectly even oil coverage, three points were measured on each coupon and the average of those three points is shown in the graph 150. A substantially linear relationship is shown between the oil on the coupons and the infrared absorbance ratio at 3.4 microns to 8.1 microns. The uncontaminated coupon is shown as zero on the contamination scale.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method of measuring a characteristic of a coating on a substrate, the method comprising:
    transmitting an infrared beam into a crystal in contact with a coating on a substrate;
    reflecting the infrared beam within the crystal;
    detecting the reflected infrared beam at a first wavelength and a second wavelength that is different from the first wavelength;
    comparing infrared energy $I_{c1}$ of the reflected infrared beam at the first wavelength with a predetermined value of infrared energy $I_{o1}$ of a reflected infrared beam at the first wavelength that is reflected within a reference crystal that is not in contact with the coating to determine an absorbance value A1 for the coating at the first wavelength;
    comparing infrared energy $I_{c2}$ of the reflected infrared beam at the second wavelength with a predetermined value of infrared energy $I_{o2}$ of a reflected infrared bean at the second wavelength that is reflected within the reference crystal that is not in contact with the coating to determine an absorbance value A2 for the coating at the second wavelength; and
    correlating a relationship between A1 and A2 to a measurement of a characteristic of the coating.

2. The method of claim 1, wherein the relationship includes a ratio between A1 and A2.

3. The method of claim 1, wherein the relationship includes a difference between A1 and A2.

4. The method of claim 1, wherein the characteristic includes an amount of cure.

5. The method of claim 4, wherein the first wavelength is in a range from about 4.21 μm to about 4.81 μm, and the second wavelength is in a range from about 5.62 μm to about 6.02 μm.

6. The method of claim 5, wherein the first wavelength is about 4.61 μm and the second wavelength is about 5.82 μm.

7. The method of claim 6, wherein the first wavelength is about 6.86 μm and the second wavelength is about 7.34 μm.

8. The method of claim 1, wherein the characteristic includes an amount of contamination.

9. The method of claim 8, wherein the first wavelength is in a range from about 6.3 μm to about 6.5 μm, and the second wavelength is in a range from about 3.37 μm to about 3.47 μm.

10. The method of claim 9, wherein the first wavelength is about 6.4 μm and the second wavelength is about 3.42 μm.

11. The method of claim 8, wherein the first wavelength is in a range from about 6.3 μm to about 6.5 μm, and the second wavelength is in a range from about 9.0 μm to about 10.0 μm.

12. The method of claim 11, wherein the first wavelength is about 6.4 μm and the second wavelength is about 9.5 μm.

13. The method of claim 8, wherein the first wavelength is about 8.1 μm and the second wavelength is about 3.4 μm.

14. The method of claim 8, wherein the first wavelength is about 8.1 μm and the second wavelength is about 9.5 μm.

15. The method of claim 1, wherein the value A1 is calculated according to the equation $A1=-\log_{10}(I_{c1}/I_{o1})$; and wherein the value A2 is calculated according to the equation $A2=-\log_{10}(I_{c2}/I_{o2})$.

16. The method of claim 1, wherein the coating includes polyurethane paint.

17. A non-destructive method of determining an amount of cure of a coating on a substrate, the method comprising:

transmitting an infrared beam into a crystal in contact with a coating on a substrate;

reflecting the infrared beam within the crystal;

detecting the reflected infrared beam at a first wavelength and a second wavelength that is different from the first wavelength;

comparing infrared energy $I_{c1}$ of the reflected infrared beam at the first wavelength with a predetermined value of infrared energy $I_{o1}$ of a reflected infrared beam at the first wavelength that is reflected within a reference crystal that is not in contact with the coating to determine an absorbance value A1 for the coating at the first wavelength according to the equation $A1=-\log_{10}(I_{c1}/I_{o1})$;

comparing infrared energy $I_{c2}$ of the reflected infrared beam at the second wavelength with a predetermined value of infrared energy $I_{o2}$ of a reflected infrared beam at the second wavelength that is reflected within the reference crystal that is not in contact with the coating to determine an absorbance value A2 for the coating at the second wavelength according to the equation $A2=-\log_{10}(I_{c2}/I_{o2})$; and correlating a relationship between A1 and A2 to an amount of cure of the coating.

18. The method of claim 17, wherein the relationship includes a ratio between A1 and A2.

19. The method of claim 17, wherein the relationship includes a difference between A1 and A2.

20. The method of claim 17, wherein the first wavelength is in a range from about 4.21 μm to about 4.81 μm and the second wavelength is in a range from about 5.62 μm to about 6.02 μm.

21. The method of claim 20, wherein the first wavelength is about 4.61 μm and the second wavelength is about 5.82 μm.

22. The method of claim 17, wherein the first wavelength is about 6.86 μm and the second wavelength is about 7.34 μm.

23. The method of claim 17, wherein the coating includes polyurethane paint.

24. A non-destructive method of determining an amount of contamination on a substrate, the method comprising:

transmitting an infrared beam into a crystal in contact with a coating on a substrate;

reflecting the infrared beam within the crystal;

detecting the reflected infrared beam at a first wavelength and a second wavelength that is different from the first wavelength;

comparing infrared energy $I_{c1}$ of the reflected infrared beam at the first wavelength with a predetermined value of infrared energy $I_{o1}$ of a reflected infrared beam at the first wavelength that is reflected within a reference crystal that is not in contact with the coating to determine an absorbance value A1 for the coating at the first wavelength according to the equation $A1=-\log_{10}(I_{c2}/I_{o2})$;

comparing infrared energy $I_{c2}$ of the reflected infrared beam at the second wavelength with a predetermined value of infrared energy $I_{o2}$ of a reflected infrared beam at the second wavelength that is reflected within the reference crystal that is not in contact with the coating to determine an absorbance value A2 for the coating at the second wavelength according to the equation $A2=-\log_{10}(I_{c2}/I_{o2})$; and correlating a relationship between A1 and A2 to an amount of contamination in the coating.

25. The method of claim 24, wherein the relationship includes a ratio between A1 and A2.

26. The method of claim 24, wherein the relationship includes a difference between A1 and A2.

27. The method of claim 24, wherein the first wavelength is in a range from about 6.3 μm to about 6.5 μm, and the second wavelength is in a range from about 3.37 μm to about 3.47 μm.

28. The method of claim 24, wherein the first wavelength is about 6.4 μm and the second wavelength is about 3.42 μm.

29. The method of claim 24, wherein the first wavelength is in a range from about 6.3 μm to about 6.5 μm, and the second wavelength is in a range from about 9.0 μm to about 10.0 μm.

30. The method of claim 29, wherein the first wavelength is about 6.4 μm and the second wavelength is about 9.5 μm.

31. The method of claim 24, wherein the first wavelength is about 8.1 μm and the second wavelength is about 3.4 μm.

32. The method of claim 24, wherein the first wavelength is about 8.1 μm and the second wavelength is about 9.5 μm.

33. The method of claim 24, wherein the contamination includes at least one of silicone, polytetrafluroethylene, hydraulic oil, lubricant, and engine oil, aircraft fuel, and cutting oil.

* * * * *